United States Patent [19]

Erlebacher

[11] Patent Number: 4,957,118
[45] Date of Patent: Sep. 18, 1990

[54] ELECTRODE LEAD

[76] Inventor: Jay Erlebacher, 55 Woodland Park Dr., Tenafly, N.J. 07670

[21] Appl. No.: 144,487

[22] Filed: Jan. 15, 1988

[51] Int. Cl.$^5$ ............................................. A61N 1/00
[52] U.S. Cl. ................................... 128/785; 128/786
[58] Field of Search ............. 128/419 P, 419 PG, 785, 128/786, 783, 784, 345, 92 YW; 604/105–110; 135/25

[56] References Cited

U.S. PATENT DOCUMENTS 4,632,101  12/1986  Freedland ...................... 128/92 YW

*Primary Examiner*—Robert A. Hafer
*Assistant Examiner*—Michael Brown
*Attorney, Agent, or Firm*—Kenyon & Kenyon

[57] ABSTRACT

The electrode lead is provided with a tine assembly having tines which can be actively moved back and forth between a retracted position and an extended position. The tines are mounted on an electrode tip which is movable relative to an elongated tubular body and are fixed to the body so that upon movement of the tip relative to the body, the tines can be moved between the retracted and extended positions. A threaded rod which is rotatably mounted within the elongated body is used to move the conductive electrode tip relative to the non-conductive tubular body.

27 Claims, 3 Drawing Sheets

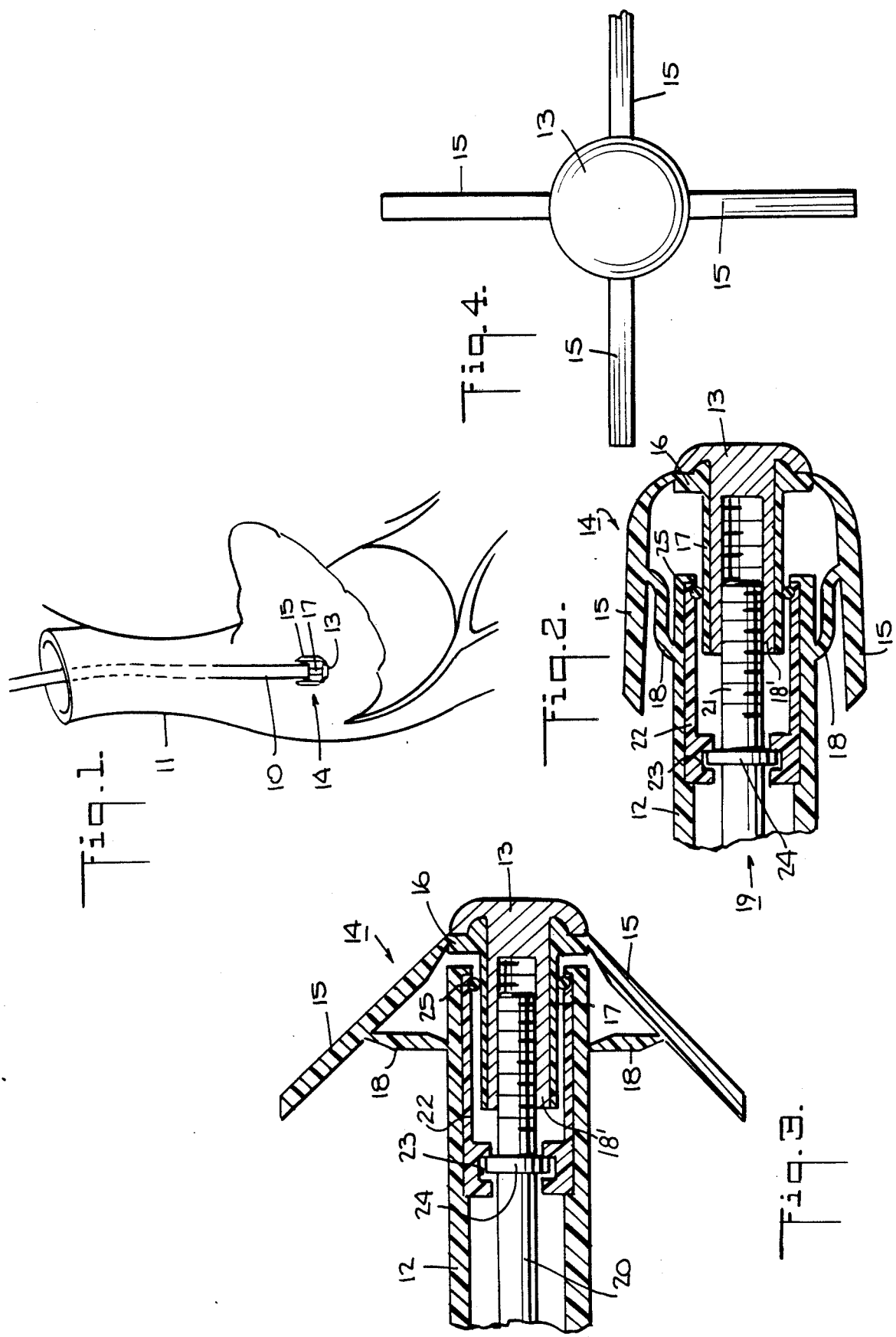

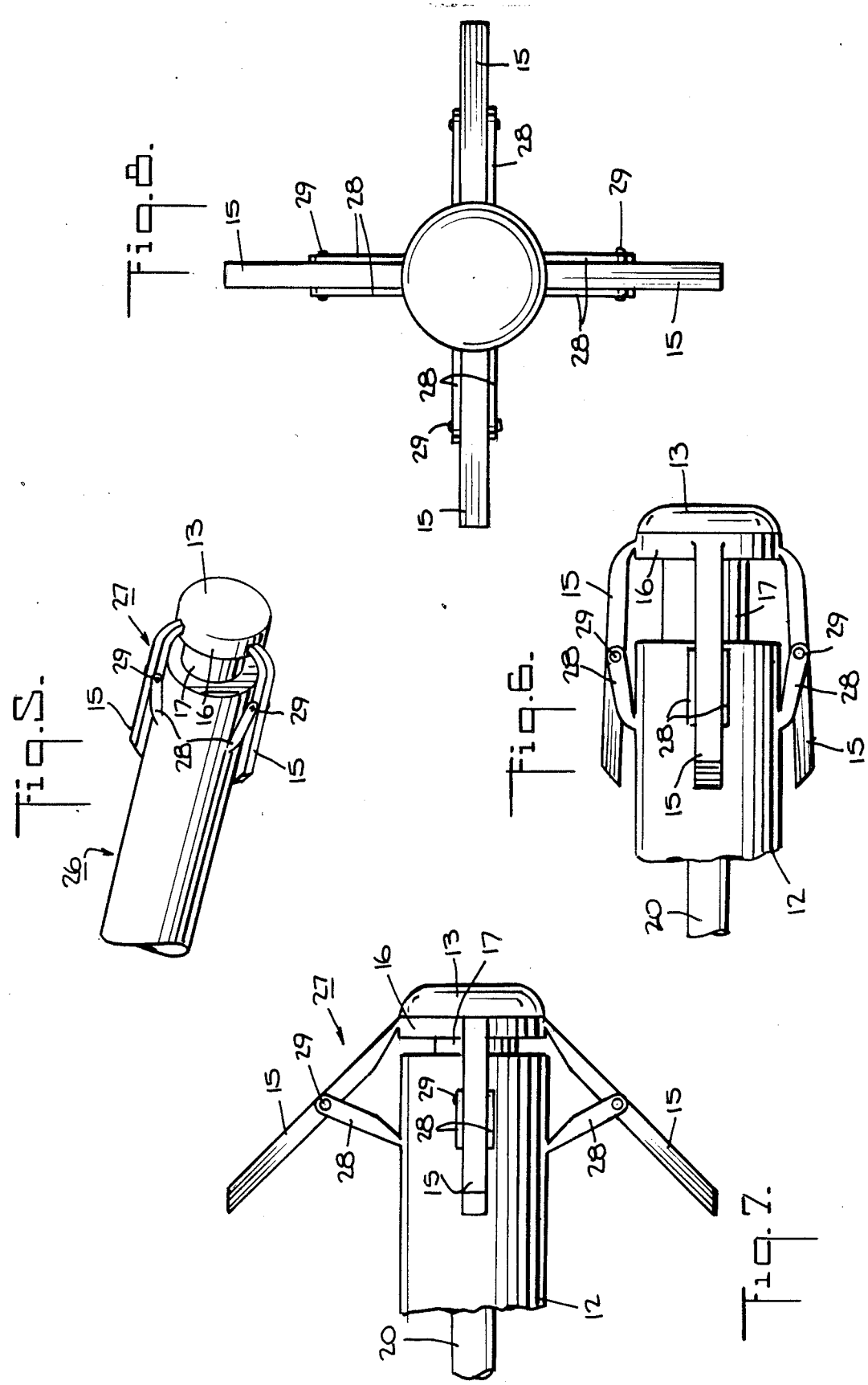

ELECTRODE LEAD

This invention relates to an electrode lead. More particularly, this invention relates to a pacemaker electrode lead.

Heretofore, various types of electrode leads have been provided for stimulating cardiac action and various arrangements have been used to secure the tips of the leads endocardial. For example, U.S. Pat. No. 3,902,501 describes an endocardial electrode which is to be used as an atrial endocardial electrode and which employs a plurality of tines for attachment to body tissue, particularly the trabeculae of the right atrial appendage in order to maintain a tip of the electrode in electrical contact with the body tissue. These tines are made of a pliable material and are maintained in angular relation to the electrode when in an unrestrained position so that during movement of the electrode through a vessel the tines depress towards the electrode proper. However, because of the inherent spring-like nature of the tines, any proximal movement of the electrode would cause the tines to spring outwardly and penetrate into the wall of the vessel or the heart, interfering with manipulation and positioning of the lead tip. Further, since actively moved back and forth the tines frequently hook onto the chordae tendineae of the tricuspid valve, the trabeculations of the right ventricle, and other assorted structures. This produces a great deal of wasted motion, time, and effort. Since this lead manipulation is done fluoroscopically, it also results in increased radiation exposure for the patient and the cardiologist.

U.S. Pat. No. 3,939,843 describes a transvenous electrode which provides a plurality of tines in a particular angular position relative to a transverse direction in order to bias the electrode in that direction. However, the tines are mounted and constructed in a manner similar to that described in U.S. Pat. No. 3,902,501 and possess similar disadvantages.

U.S Pat. No. 4,409,994 describes a lap joint molding member for a pacemaker electrode lead which employs flexible tines which can be recessed in a molding member during distal movement of the lead. However, these tines also present similar problems as in the above noted leads should a proximal movement occur.

Accordingly, it is an object of the invention to allow unhindered intra-operative manipulation of an electrode lead.

It is another object of the invention to simplify the implantation of an endocardial electrode lead.

It is another object of the invention to provide an electrode lead of simplified construction for cardiac implantation.

Briefly, the invention provides an electrode lead which comprises an elongated tubular body sized for passage through a vessel, an electrically conductive tip mounted at a distal end of the body, a tine assembly with a plurality of tines for movement between a retracted position towards the body and an extended position away from the body and means extending within the body and connected to the tip for moving the tip relative to the body to cause the tines to move between the retracted position and extended position.

The tine assembly is constructed so that the tines are fixedly secured at one end relative to the tip and movably secured at intermediate points relative to the body so as to be moved between the extended and retracted positions in response to movement of the tip relative to the elongated body. To this end, the tine assembly includes a plurality of struts which are connected to and between the tines and the body for moving the tines.

In one embodiment, each strut is integral with a respective tine while being secured to the elongated body. In another embodiment, pairs of struts are pivotally connected to each tine as well as to the body.

The tine assembly may also include a sleeve which is mounted about a stem of the tip and which is integral with the tines. This sleeve may project into the elongated body with a sealing ring being disposed between the sleeve and the body in order to preclude entry of fluids into the interior of the body.

The means for moving the tip relative to the body includes an actuating rod which is rotatably mounted within the body in fixed axial relation and which has a threaded end threadably received in the tip. This construction permits the tip to be moved axially relative to the body in response to rotation of the actuating rod within the actuating body. Further, the rod is electrically conductive and is electrically connected to the tip to conduct an electrical impulse to the tip when required.

When the electrode lead is being passed through the veins and heart electrode leads are often advanced into the heart with the tined tip of the lead trailing the lead body to the apex of the right ventricle, the tines of the tine assembly are held in the retracted position against the outside surface of the elongated body. This presents a minimum cross-section to facilitate passage of the electrode lead through the vessel. Further, the retracted tines allow the lead to be manipulated into the heart with the tip trailing in an unhindered way. Once the tip has been brought into a position to be in electrical contact with the endocardial tissue, the tip and elongated body can be moved relative to each other by turning of the actuating rod, for example from the proximal end of the lead. At this time, as the tip moves inwardly relative to the body, the tines are guided into the extended position so as to engage with the trabeculae and thus hold the tip against movement away from the endocardial tissue.

Since the tines need not be extended until the tip has reached the final desired position, manipulative movements may be readily made of the tip without the tines engaging in the surrounding tissue. Further, should the tip need to be repositioned once the tines have been extended, the tines may again be retracted to facilitate unentered movement of the lead within the heart.

These and other objects and advantages of the invention will become more apparent from the following detailed description taken in conjunction with the accompanying drawings wherein:

FIG. 1 illustrates a perspective view of an electrode lead constructed in accordance with the invention being passed through a vessel;

FIG. 2 illustrates a cross-sectional view of the tine assembly in the retracted position in accordance with the invention;

FIG. 3 illustrates a cross-sectional view of the tine assembly in an extended position in accordance with the invention;

FIG. 4 illustrates an end view of the electrode lead with the tines in an extended position;

FIG. 5 illustrates a part perspective view of a modified tine assembly in accordance with the invention;

FIG. 6 illustrates a side view of the electrode lead of FIG. 5;

FIG. 7 illustrates a view similar to FIG. 6 of the tine assembly with the tines in an extended position; and FIG. 8 illustrates a front view of the electrode lead of FIG. 5 with the tines in the extended position.

Referring to FIG. 1, the electrode lead 10 is constructed so as to be passed through a vessel for implantation in a chamber of a heart 11. As indicated, the electrode lead 10 includes an elongated tubular non-conductive body 12 which is made of any suitable material and flexibility for passage into the heart 11. In addition, the lead 10 includes an electrically conductive tip 13 which is mounted at the distal end of the body 12 and a tine assembly 14 which is mounted on the tip 13 in order to secure the tip 13 in electrical contact with the endocardial tissue of the heart (not shown)

Referring to FIG. 2, the tine assembly 14 includes a plurality of tines 15, for example four, which are fixedly secured at a distal end to a ring-shaped annular flange 16 of a sleeve 17 as well as a plurality of struts 18 which are connected to and between the tines 15 and the body 12. The tines 15 may be secured to the flange 16 of the sleeve 17 in any suitable manner. For example, the tines 15 may be integrally formed with the flange 16 and, likewise, may be integral with the struts 18. For example, the tine assembly 14 constituted by the tines 15, flanged sleeve 17 and struts 18 may be molded of a plastic material, such as polyurethane, silicone, and the like, in a one-piece unit. In this case, the tines 15 are flexible while both the tines 15 and sleeve 16 are non-conductive.

Alternatively, the tines 15 may be secured to the annular flange 16 by an adhesive. As shown in FIG. 4, the tines 15 are equi-spaced circumferentially about the tip 13.

As indicated in FIG. 2, the tip 13 has a stem 18 which extends into and within the proximal end of the body 12. and receives the sleeve 17 thereon in coaxial manner. The tip 13 is also suitably recessed to receive the annular flange 16 such that the sleeve 17 and stem 18 are movable as a unit.

A means 19 also extends within the body 12 and is connected to the tip 13 for moving the tip 13 relative to the body 12 in order to cause the tines 15 to move between a retracted position as shown in FIG. 2 and an extended position as shown in FIGS. 3 and 4. In this respect, the means includes a screw mechanism having a actuating 20 rotatably mounted within the body 12 in fixed axial relation. The rod 20 includes a threaded distal end 21 which is threadably received within a threaded bore of the stem 18 of the tip 13 such that the tip 13 is axially movable relative to the body 12 in response to rotation of the actuating rod 20 within the body 12. As indicated, a rigid cylinder 22 is coaxially mounted in fixed relation within the distal end of the body 12 and forms an internal annular recess 23 to rotatable receive an annular collar 24 which is fixed on the actuating rod 20 so as to limit axial movement between the rod 20 and the body 12. In addition, a sealing ring 25 is disposed in sealing relation between the cylinder 21 and the sleeve 17 of the tine assembly 14 in order to preclude entry of fluid into the interior of the body 12.

The actuating rod 20 is connected at the proximal end to any suitable actuating means (not shown) to cause rotation of the actuating rod 20 relative to the body 12. In addition, the actuating rod 20 is electrically conductive to transmit electrical signals from a suitable source to the tip 13.

The rigid cylinder 22 imparts sufficient rigidity to the distal end of the body 12 to stabilize and fix the position of the threaded connection between the actuating rod 20 and the tip 13 in order to permit relative movement between the tip 13 and the body 12.

As indicated in FIGS. 1 and 2, during passage through a vessel and heart 11, the tine assembly 14 is in the retracted position. When the electrode tip 13 is in the final desired position, the actuating rod 20 is rotated so as to cause relative movement between the tip 13 and the body 12, that is, the tip 13 moves relatively inwardly into the body 12. At the same time, the tines 15 are caused to move radially outwardly via the struts 18 into the extended position as shown in FIG. 3 in order to engage with the trabeculae and hold the tip 13 in electrical contact with the endocardial tissue.

As indicated in FIGS. 2 and 3, the proximal end of each tine 15 is beveled so as to provide a sharp point which can penetrate between trabeculae in response to a proximal movement of the electrode lead 10 after the tines 15 have been extended. However, as indicated in FIG. 1, the bevel is such as to facilitate distal and proximal movement through a vessel or heart 11 without hindrance with the tines retracted.

The materials from which the electrode lead 10 may be made should be compatible with body tissue.

Referring to FIG. 5, wherein like reference characters indicate like parts as above, the electrode lead 26 may be constructed with a tine assembly 27 in which the struts 28 are disposed in pairs and pivotally connected to a respective tine 15 via a pin 29. The struts 28 may also be pivotally connected in a similar fashion to the elongated tubular body 12 or may be integral with the body 12 or the tines 15.

As indicated in FIG. 6, when in a retracted position, the tines 15 lay flat against the body 12 and, thus, provide a lower cross-sectional profile. When the actuating rod 20 is rotated, the tines 15 can be moved to the extended position indicated in FIGS. 7 and 8 under the guidance of the struts 28.

It is to be noted that various modifications may be made in the electrode lead for various purposes. For example, in order to reduce the profile of the lead in the retracted position for passage through a vessel, the body 12 may be recessed to receive the struts 18 and tines 15. Likewise, the circumferential arrangement of the tines 15 may be other than an equi-spaced arrangement as indicated in each of FIGS. 4 and 8. Radio-opaque markers may also be placed in the tines 15 in order to allow X-ray fluoroscopic visualization as to whether the tines 15 are extended or retracted.

The invention thus provides an electrode lead which can be readily manipulated during implantation with the tines positively held in a retracted position. Further, the invention provides a positive means for extending the anchoring tines of the electrode lead to insure secure mounting in body tissue. Still further, the retractable tines allow the motion of the lead tip in a retrograde manner without hindrance from the intracardiac structures. Once the lead tip is at the right ventricular apex, the tines are extended so that they catch on the trabeculae and prevent displacement of the lead tip.

What is claimed is:

1. An electrode lead comprising
an elongated tubular body;
an electrically conductive tip mounted in a distal end of said body;

a plurality of tines disposed about said tip, each said tine being fixedly secured at one end relative to said tip;

a plurality of struts connected to and between said tines and said body to permit movement of said tines between a retracted position towards said body and an extended position away from said body; and means extending within said body and connected to said tip for moving said tip relative to said body to cause said tines to move between said positions.

2. An electrode lead as set forth in claim 1 wherein each strut is integral with a respective tine.

3. An electrode lead as set forth in claim 1 wherein each strut is pivotally connected to a respective tine and to said body.

4. An electrode lead as set forth in claim 1 wherein said tip has a hollow stem extending coaxially within said body and which further comprises a non-conductive sleeve mounted on and about said stem and having said tines integral therewith.

5. An electrode lead as set forth in claim 4 wherein said sleeve and said tines are made of plastic.

6. An electrode lead as set forth in claim 1 wherein said means includes an actuating rod rotatably mounted within said body in fixed axial relation therewith, said rod having a threaded end threadably received in said tip whereby said tip is axially movable relative to said body in response to rotation of said rod within said body.

7. An electrode lead as set forth in claim 6 which further comprises a rigid cylinder within a distal end of said body having an internal annular recess and an annular collar on said rod rotatably received within said recess to limit axial movement between said rod and said body.

8. An electrode lead as set forth in claim 7 wherein said tip has a stem extending within said body and which further comprises a sleeve mounted on and about said stem and having said tines integral therewith.

9. An electrode lead as set forth in claim 8 which further comprises a sealing ring between said cylinder and said sleeve.

10. An electrode lead as set forth in claim 1 which further comprises a sealing ring between said tip and said body.

11. An electrode lead comprising an elongated tubular body for passage through a vessel;

an electrically conductive tip mounted at a distal end of said body;

a tine assembly mounted on said tip and including a plurality of tines fixedly secured at one end thereof relative to said tip and movably secured at an intermediate point thereof relative to said body for movement between a retracted position against said body and an extended position away from said body; and means extending within said body and connected to said tip for moving said tip relative to said body to cause said tines to move between said positions.

12. An electrode lead as set forth in claim 11 wherein said tine assembly includes a plurality of struts connected to and between said tines and said body for moving said tines between said positions during relative movement between said tip and said body.

13. An electrode lead as set forth in claim 12 wherein each strut is integral with a respective tine.

14. An electrode lead as set forth in claim 12 wherein each strut is pivotally connected to a respective tine and to said body.

15. An electrode lead as set forth in claim 11 wherein said means is electrically conductive and is electrically connected to said tip.

16. An electrode lead as set forth in claim 11 wherein said means includes a rod rotatably mounted within said body in fixed axial relation therewith, said rod having a threaded end threadably received in said tip whereby said tip is axially movable relative to said body in response to rotation of said rod within said body.

17. An electrode lead as set forth in claim 16 which further comprises a rigid cylinder within a distal end of said body having an internal annular recess and an annular collar on said rod rotatably received within said recess to limit axial movement between said rod and said body.

18. An electrode lead as set forth in claim 11 wherein said tip has a hollow stem extending coaxially within said body and which further comprises a non-conductive sleeve mounted on and about said stem and having said tines integral therewith.

19. An electrode lead as set forth in claim 18 which further comprises a sealing ring between said sleeve and said body.

20. In an electrode lead, the combination comprising an elongated tubular body;

an electrically conductive tip at a distal end of said body;

a tine assembly including a plurality of tines mounted on said tip for movement between a retracted position against said body and an extended position away from said body; and means connecting said tines at intermediate points thereof to said body; and means extending within said body for moving said tines between said positions.

21. The combination as set forth in claim 20 wherein said means is connected to said tip for moving said tip relative to said body to cause said tines to move between said positions.

22. The combination as set forth in claim 21 wherein said tines are movable longitudinally with respect to said body.

23. In an electrode lead, the combination comprising an elongated tubular body;

an electrically conductive tip at a distal end of said body;

a plurality of tines mounted for movement between a retracted position against said body and an extended position away from said body to secure said tip in electrical contact with endocardial tissue;

means connecting said tines at intermediate points thereof to said body; and means extending within said body for moving said tines between said positions.

24. The combination as set forth in claim 23 wherein said tines are integrally connected for simultaneous movement between said positions.

25. The combination as set forth in claim 23 wherein said tines are equispaced about said tip.

26. The combination as set forth in claim 23 wherein each tine has a beveled proximal end to provide a sharp point to penetrate between trabeculae.

27. The combination as set forth in claim 23 wherein said tines lay flat against said body in said retracted position.

* * * * *

UNITED STATES PATENT AND TRADEMARK OFFICE
CERTIFICATE OF CORRECTION

PATENT NO. : 4,957,118

DATED : Sept. 18, 1990

INVENTOR(S) : JAY ERLEBACHER

It is certified that error appears in the above-identified patent and that said Letters Patent is hereby corrected as shown below:

```
Column 1, line 10 after "leads" insert -to the-
Column 2, line 26, change "actively ... forth" to -electrode leads
are often advanced into the heart with the tined tip of the lead
trailing the lead body,-
Column 3, line 36 change "18" to -18'-
Column 3, line 40 change "18" to -18'-
Column 3, line 51 change "18" to -18'-
Column 3, line 48 after "actuating" insert -rod-
Column 6, line 33 cancel "and"
Column 3, line 20 after "12." insert -As illustrated in Figs. 2
and 3, each strut 18 serves as a means for connecting a
respective time 15 at an intermediate point thereof to the body
12.
```

Signed and Sealed this

Twelfth Day of May, 1992

Attest:

DOUGLAS B. COMER

*Attesting Officer*      *Acting Commissioner of Patents and Trademarks*